United States Patent
Oliveira Sumner et al.

(10) Patent No.: US 12,055,551 B2
(45) Date of Patent: Aug. 6, 2024

(54) METHODS FOR MITIGATING DRUG TARGET INTERFERENCE IN AN ANTI-DRUG ANTIBODY (ADA) IMMUNOASSAY

(71) Applicant: Regeneron Pharmaceuticals, Inc., Tarrytown, NY (US)

(72) Inventors: Giane Oliveira Sumner, Tarrytown, NY (US); Jihua Chen, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 756 days.

(21) Appl. No.: 16/506,379

(22) Filed: Jul. 9, 2019

(65) Prior Publication Data
US 2020/0018770 A1  Jan. 16, 2020

Related U.S. Application Data

(60) Provisional application No. 62/696,016, filed on Jul. 10, 2018.

(51) Int. Cl.
| | | |
|---|---|---|
| *G01N 33/53* | (2006.01) | |
| *G01N 33/577* | (2006.01) | |
| *G01N 33/58* | (2006.01) | |
| *G01N 33/68* | (2006.01) | |
| *G01N 33/94* | (2006.01) | |

(52) U.S. Cl.
CPC ....... *G01N 33/6854* (2013.01); *G01N 33/577* (2013.01); *G01N 33/58* (2013.01); *G01N 33/94* (2013.01)

(58) Field of Classification Search
CPC ............ G01N 33/577; G01N 33/5306; G01N 33/6854; G01N 33/58; G01N 33/94
See application file for complete search history.

(56) References Cited

U.S. PATENT DOCUMENTS

| | | |
|---|---|---|
| 3,856,469 A | 12/1974 | Schneider et al. |
| 2006/0281132 A1 | 12/2006 | Kitawaki et al. |
| 2015/0226758 A1 | 8/2015 | Grabert et al. |
| 2019/0145985 A1 | 5/2019 | Zemo et al. |
| 2021/0293811 A1* | 9/2021 | Chen ................ G01N 33/54306 |

FOREIGN PATENT DOCUMENTS

| | | |
|---|---|---|
| CN | 104203975 A | 12/2014 |
| CN | 105378480 A | 3/2016 |
| JP | 2-138872 A | 5/1990 |
| JP | 2010-527005 A | 8/2010 |

(Continued)

OTHER PUBLICATIONS

Chen et al., Mitigating target interference in bridging immunogenicity assay with target-blocking reagents and mild basic pH. Bioanalysis. Sep. 2019; 11(17):1569-1580.

(Continued)

*Primary Examiner* — Shafiqul Haq
(74) *Attorney, Agent, or Firm* — McCarter & English, LLP; Maria Laccotripe Zacharakis

(57) ABSTRACT

The present disclosure provides methods for mitigating drug target interference in an anti-drug antibody (ADA) immunoassay, wherein the ADA immunoassay comprises one or more target blocking reagents under mild basic pH assay conditions.

23 Claims, 11 Drawing Sheets

(56) References Cited

FOREIGN PATENT DOCUMENTS

| JP | 2016-530495 | A  | 9/2016 |
|----|-------------|----|--------|
| JP | 64-54356    | B2 | 1/2019 |
| WO | 2005/031353 | A1 | 4/2005 |
| WO | 2009/022001 | A1 | 2/2009 |
| WO | 2019/105916 | A1 | 6/2019 |

OTHER PUBLICATIONS

Dai et al., Development of a method that eliminates false-positive results due to nerve growth factor interference in the assessment of fulranumab immunogenicity. AAPS J. May 2014;16(3):464-77.

Liao et al., Inhibition of interleukin-5 induced false positive anti-drug antibody responses against mepolizumab through the use of a competitive blocking antibody. J Immunol Methods. Feb. 2017;441:15-23.

International Search Report and Written Opinion for Application No. PCT/US2019/040950, dated Sep. 30, 2019, 12 pages.

Collet-Brose et al., Evaluation of Multiple Immunoassay Technology Platforms to Select the Anti-Drug Antibody Assay Exhibiting the Most Appropriate Drug and Target Tolerance. J Immunol Res. 2016;2016:5069678.

Chen et al., False-positive immunogenicity responses are caused by CD20+ B cell membrane fragments in an anti-ofatumumab antibody bridging assay. J Immunol Methods. Aug. 30, 2013;394(1-2):22-31.

\* cited by examiner

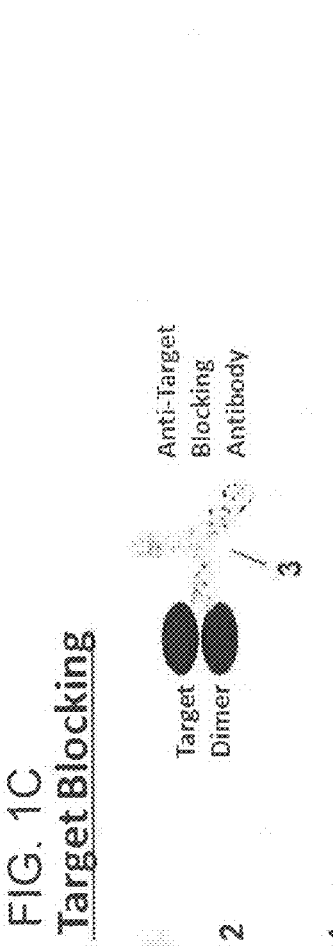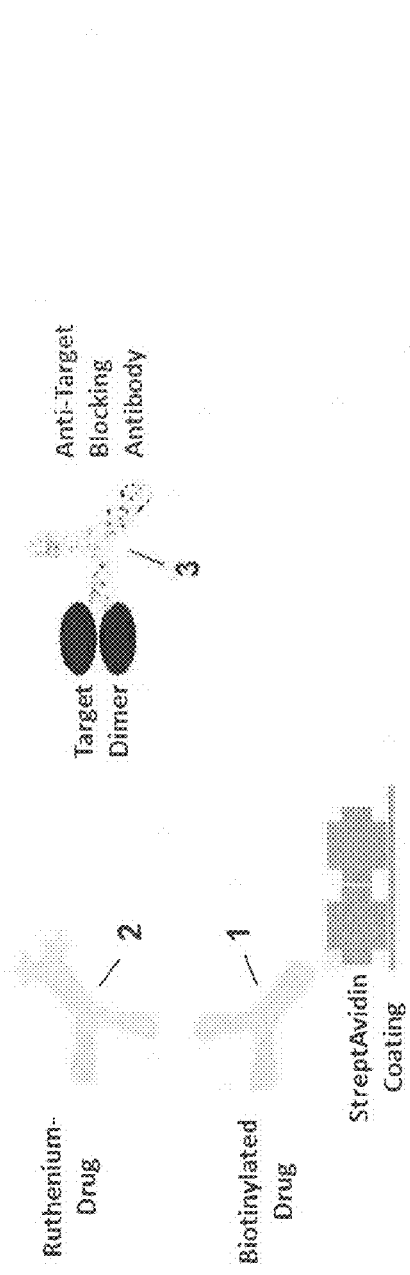
FIG. 1A ADA Detection (True Positive)
FIG. 1B Target Interference (False Positive)
FIG. 1C Target Blocking ADA Signal Increased with Acid Treatment Target Tolerance Level Improved with HuAb1 and pH 8.3

Reduction of Target-Mediated Background Signal with HuAb1 and pH 8.3

Target Concentration in Clinical Samples

ADA Signal in Clinical Samples

Drug X Concentration in Clinical Samples

Additional Anti-Target Antibody HuAb2 Reduced Background Signal in Clinical Samples Signal:Background ADA Signal in Clinical Samples with MsAb2, MsSR and pH 8.3

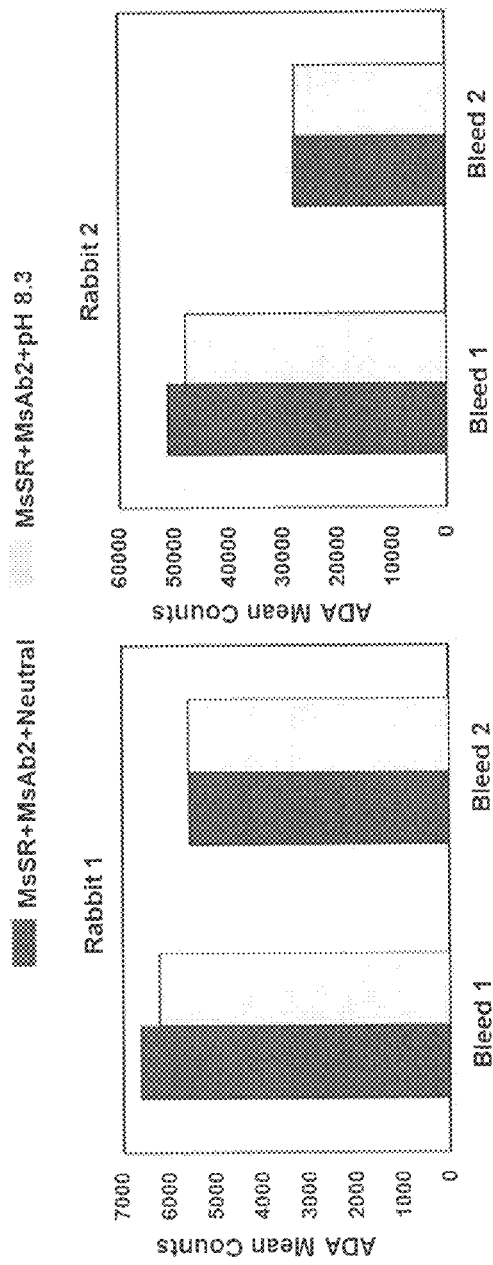

Real ADA Signal Detection in Rat Toxicology Samples

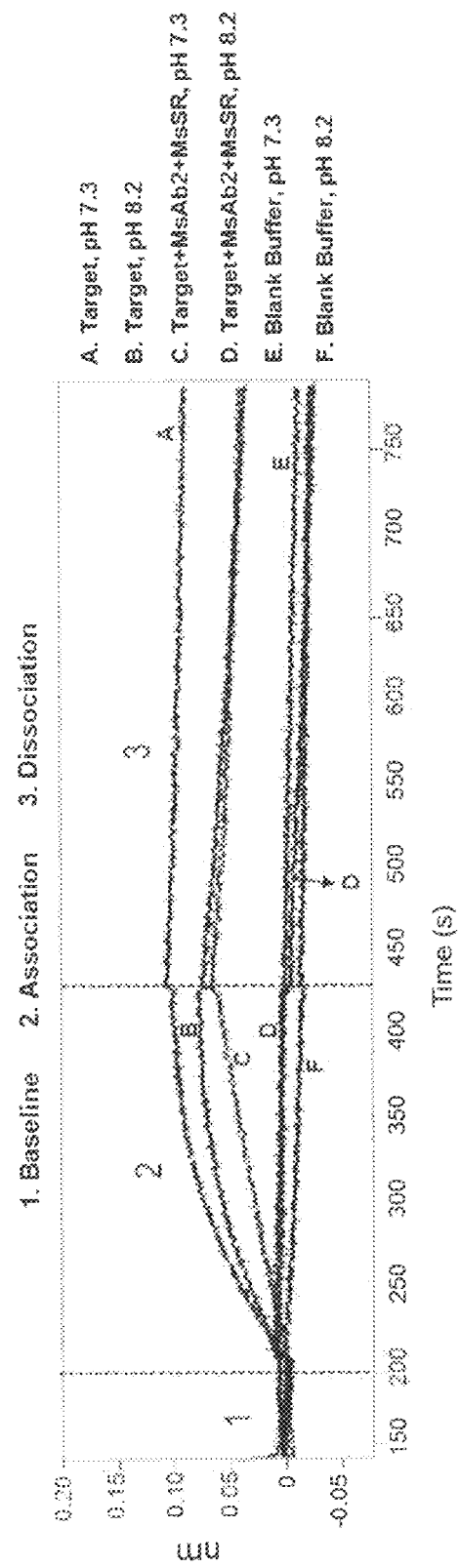

Effect of pH on ADA Signal Observed from Clinical Samples, in the Absence or Presence of MsAb2 and MsSR

METHODS FOR MITIGATING DRUG TARGET INTERFERENCE IN AN ANTI-DRUG ANTIBODY (ADA) IMMUNOASSAY

REFERENCE TO RELATED APPLICATIONS

This application claims the benefit of priority to U.S. provisional application Ser. No. 62/696,016, filed on Jul. 10, 2018. The entire contents of the foregoing application are incorporated herein by reference.

BACKGROUND

Biotherapeutics (e.g., biologic agents such as proteins, peptides, nucleotides, etc.) have proven very successful in clinical practice. However, biotherapeutics, even fully human therapeutic monoclonal antibodies, have the potential to generate anti-drug antibodies (ADAs) that can cause undesired effects such as loss of drug exposure, loss of efficacy and serious adverse events, etc. (Koren, E., et al. Curr Pharm Biotechnol, 2002, 3(4): p. 349-60; Schellekens, H., Clin Ther, 2002, 24(11): p. 1720-40). Therefore, immunogenicity assessment is an important part of the safety testing for biotherapeutics, with several issued recommendations on immunogenicity testing during various stages of drug development, including those from regulatory agencies (Shankar, G., et al., J Pharm Biomed Anal, 2008, 48(5): p. 1267-81; Shankar, G., et al. Nat Biotechnol, 2007, 25(5): p. 555-61; Mire-Sluis, A. R., et al., J Immunol Methods, 2004, 289(1-2): p. 1-16; Swanson, S. J. and J. Bussiere, Curr Opin Microbiol, 2012, 15(3): p. 337-47; European Medicines Agency, C.f.M.P.f.H.U., *Guideline on Immunogenicity Assessment of Biotechnology-Derived Therapeutic Proteins*. European Medicines Agency, London, U K, 2007; and US Department of Health and Human Services, U.F.C., CBER, *Guidance for Industry—Assay Development for Immunogenicity Testing of Therapeutic Proteins (Draft)*. US Department of Health and Human Services, Washington, DC, USA, 2009).

SUMMARY

The present invention is directed to methods for mitigating drug target interference in an anti-drug antibody (ADA) bridging immunoassay used for the determination of the presence of an ADA against a drug in a serum sample. The instant methods comprise contacting the serum sample with a capture drug labelled with a first label; a detection drug labelled with a second label; and a drug target blocking reagent. This contacting step is then followed by incubating the capture drug, the detection drug, and the drug target blocking reagent allowing the drug target blocking reagent to interact with the drug target present in the sample, thereby mitigating the interference of the drug target in the ADA bridging immunoassay. This may be followed by performing an anti-drug antibody (ADA) bridging immunoassay.

In one aspect of the present invention, the serum sample is a human serum sample and in a particular aspect, the sample is from a subject being treated with the drug.

In another aspect, the drug target blocking reagent is a binding molecule such as, e.g., an antibody. In one embodiment, wherein the binding molecule is an antibody, it may comprise a human constant region. Alternatively, in another embodiment, the drug target blocking antibody comprises a mouse constant region.

In one aspect, the incubation step is performed at room temperature. In another aspect, the incubation is carried out under mild basic pH conditions.

In one aspect, the drug of the present invention is a therapeutic protein used to treat humans, such as a therapeutic binding molecule such as a monoclonal antibody (e.g., fully human monoclonal antibody) or a therapeutic fusion protein such as a receptor protein fused to an immunoglobulin Fc domain, e.g., an IgG1 Fc domain designed to treat humans. In a particular aspect, the drug is a therapeutic human monoclonal antibody.

In one aspect of the present invention, the drug target is a soluble protein such as, e.g., a ligand to a receptor. In a particular aspect, the drug target blocking reagent comprises a portion of the receptor fused to an IgG Fc domain. In a further aspect, the portion of the receptor is an extracellular portion of the receptor. The IgG Fc domain may be a mouse IgG Fc domain or a human IgG Fc domain.

In another aspect, the drug target of the present invention is a soluble or shed dimeric or multimeric drug target. In a particular aspect, the drug target is a homodimeric drug target.

In one aspect, the capture drug of the present invention is attached to a solid surface. In a particular aspect, the solid surface is a microtiter plate. In another aspect, the solid surface is coated with streptavidin.

In one aspect, the first label is selected from the group consisting of a biotin label, a Protein A label, a Protein G label, and a glutathionine S-transferase (GST) label. In another aspect, the second label is selected from the group consisting of a ruthenium label, a radiologic label, a photoluminescent label, a chemiluminescent label, a fluorescent label, an electrochemiluminescent label, and an enzyme label.

The present method may further comprise contacting the serum sample with a second drug target blocking reagent. This second drug target blocking reagent is a drug target blocking binding molecule such as, e.g., an antibody. In one aspect, the second drug target blocking antibody comprises a human constant region. Alternatively, the second drug target blocking antibody comprises a mouse constant region.

The present invention provides a method for mitigating drug target interference in an anti-drug antibody (ADA) bridging immunoassay for the determination of the presence of an ADA against a drug in a serum sample, comprising contacting the serum sample with a capture drug labelled with a first label; a detection drug labelled with a second label; a first drug target blocking binding molecule; and a second drug target blocking binding molecule, incubating under mild basic pH assay conditions the capture drug, the detection drug, the first drug target blocking binding molecule, and the second drug target blocking binding molecule, and allowing the first drug target blocking binding molecule and the second drug target blocking binding molecule to interact with the drug target present in the sample, thereby mitigating the interference of the drug target in the ADA bridging immunoassay. In a particular aspect, the first and second drug target blocking binding molecule is an antibody.

The present invention further provides a method for mitigating drug target interference in an anti-drug antibody (ADA) bridging immunoassay for the determination of the presence of an ADA against a drug in a serum sample, wherein the drug target is a soluble protein such as, e.g., a ligand to a receptor, the method comprising contacting the serum sample with a capture drug labelled with a first label; a detection drug labelled with a second label; one or more drug target blocking binding molecules (e.g., an antibody)

comprising incubating, under mild basic pH assay conditions, wherein the capture drug, the detection drug and the one or more drug target blocking binding molecules interact with the drug target present in the sample, thereby mitigating the interference of the drug target in the ADA bridging immunoassay.

The present invention is illustrated by the following drawings and detailed description, which do not limit the scope of the invention described in the claims.

BRIEF DESCRIPTION OF THE DRAWINGS

FIGS. 1A-C depict interference from soluble dimeric/multimeric target in bridging immunogenicity assays. FIG. 1A shows positive controls or ADAs in human serum samples bridge biotinylated drug and ruthenylated drug and generate a true positive ADA signal. However, FIG. 1B shows that dimeric/multimeric targets can also bind to both biotinylated drug and ruthenylated drug and generate a target-mediated false positive signal. FIG. 1C shows anti-target antibodies or other target blocking reagents can prevent the binding of dimeric target to biotinylated drug and ruthenylated drug, abrogating the target mediated false positive signal. The reagents labeled in (FIG. 1C) represent a capture drug (1), a detection drug (2), and one or more drug target blocking molecule (3).

FIG. 2A shows that without target blocking antibodies, acid dissociation increased the background assay signal in naive human serum sample possibly by releasing target from its endogenous binding proteins. FIG. 2B shows that the target tolerance level improved with addition of 100 m/mL of HuAb1 under neutral pH (from approximately 3 ng/mL to 150 ng/mL) and was further improved (to approximately 1.1 µg/mL) with the combination of HuAb1 and mild basic pH. FIG. 2C shows that the addition of 100 m/mL of HuAb1 with basic assay conditions (pH 8.3) greatly reduced the target mediated signal in naïve human serum samples.

FIG. 3A shows the target concentration for each clinical sample. FIG. 3B shows ADA signal using 100 m/mL of target blocking antibody HuAb1 and pH 8.3. FIG. 3C shows the drug X concentration profiles for the 3 subjects tested. FIG. 3D shows that the addition of a second anti-target antibody (HuAb2 at 100 m/mL) in combination with HuAb1 (100 m/mL) and mild basic pH effectively reduced the target mediated background signal in clinical samples.

FIG. 4A shows that HuSR and HuAb2 combination was as effective as HuAb1 and HuAb2 combination in mitigating target interference in clinical study samples. FIG. 4B and FIG. 4C show that target blocking reagents with mouse Fc (MsSR and MsAb2) still effectively mitigate target interference in clinical study samples.

FIGS. 6A-B depict minimal impact of mild basic assay pH and target blocking reagents on polyclonal ADA detection in immunized rabbit serum and in rat toxicology samples. FIG. 6A shows that mild basic pH 8.3 had no negative impact on ADA detection in drug Fab-immunized rabbit serum. FIG. 6B shows that improved assay format mitigates target mediated signals and detects real ADA signals in rat toxicology samples.

FIGS. 7A-B depict binding of the target to the drug in the absence and presence of target blocking reagents and with different assay pHs. FIG. 7A shows binding association and disassociation curves with different assay conditions. The wavelength shift (Δ nm) is directly proportional to the change in the thickness of the bio sensor tip as a result of target binding to the drug. The association and dissociation of the target to the drug is shown at pH 7.3 and at pH 8.2, in the presence of MsAb2 and MsSR at pH 7.3 and in the presence of MsAb2 and MsSR at pH 8.2. The buffer controls at pH 7.3 and pH 8.2 are also shown. Binding of the target to drug is partially inhibited by pH 8.3 alone. While the MsAb2 and MsSR combination with neutral assay pH can greatly reduce the binding of the target to drug, the complete inhibition of the binding is achieved with the combination MsAb2, MsSR and mild basic pH. FIG. 7A shows that target-mediated signals in clinical samples were partially inhibited by mild basic pH alone or by the presence of MsAb2 and MsSR at neutral pH. However, the complete inhibition of the target interference is achieved by the combination of MsAb2, MsSR and pH 8.3.

DETAILED DESCRIPTION

Figure 2A:
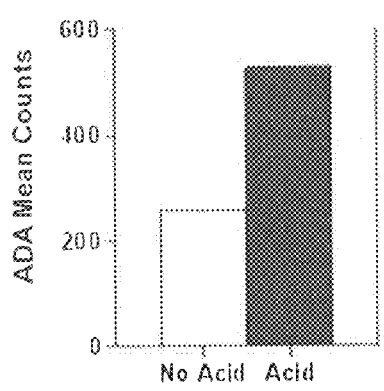
FIGS. 2A-C depict the impact of target blocking antibody HuAb1 and assay pH on assay signal.

Immunogenicity of drug products, particularly therapeutic proteins, is a major concern in clinical and preclinical studies, since it can lead to potentially serious side effects, loss of efficacy, and changes in drug exposure, complicating the interpretation of toxicity, pharmacokinetic (PK) and pharmacodynamics (PD) data. Anti-antibody drug (ADA) immunoassays to detect and quantify ADAs are important in determining immunogenicity of biotherapeutics. However, drug targets can interfere with the ADA immunoassay and result in target-mediated false positive results (see FIG. 1B). Target levels can be high based on target up-regulation and the release of target from target:drug and/or target:binding protein complexes during the acid dissociation step, usually employed in ADA assays to improve the assay drug tolerance.

ADA is usually tested in a multi-tiered approach to detect, confirm and titer ADA. The screening assay usually employs a floating cut point to identify samples that are potentially positive for ADA while the confirmation assay uses a confirmation cut point to determine if the observed positive response in the screening assay can be inhibited by the presence of excess drug (confirming the sample as positive for ADA). A titer cut point is used in the titer assay to assess levels of ADA in positive samples. ADA assays typically use a bridging format, using drugs as both capture and detection reagents. These assays are relatively easy to set up and run, detect most isotype responses, with the exception of most IgG4s, and provide excellent sensitivity. They are not species-specific and are high-throughput. However, soluble or shed dimeric- or multimeric-drug targets can interfere with the assay and result in target mediated false-positive results. For example, elevated IL-5 homodimer in post-dose samples from Mepolizumab treated patients contributed to the observed increased ADA assay positivity by generating target-mediated false positive signals in the ADA bridging assay (Liao, K., et al., J Immunol Methods, 2017, 441: p. 15-23). The presence of NGF, a homodimer, also created false positive assay signals in samples from Fulranumab dosed patients by bridging biotin and ruthenium-labeled Fulranumab (Dai, S., et al., AAPS J, 2014, 16(3): p. 464-77). CD20 present on cell membrane fragments were reported to also cause matrix interference in an ADA assay for Ofatumumab (Chen, K., et al., J Immunol Methods, 2013, 394 (1-2): p. 22-31). Furthermore, acid dissociation has recently been reported to dimerize a monomeric target in serum samples, also resulting in false positive signals (Zoghbi, J., et al., J Immunol Methods, 2015, 426: p. 62-9).

Certain methods have been reported to attempt to limit target interference. For example, pretreatment with target blocking antibodies or blocking with target-binding proteins as well as target immunodepletion has been used to mitigate soluble target interference (Liao, K., et al., J Immunol Methods, 2017, 441: p. 15-23; Dai, S., et al., AAPS J, 2014, 16(3): p. 464-77; Zhong, Z. D., et al., J Immunol Methods, 2010, 355(1-2): p. 21-8; Weeraratne, D. K., et al., J Immunol Methods, 2013, 396(1-2): p. 44-55; and Maria M, L. J., Wakshull E, Quarmby V., AAPS National Biotechnology Conference. Seattle, WA, USA, 2009). Other strategies have been reported, including the use of wheat germ agglutinin (WGA) lectin to block the interference from a highly glycosylated target protein without impacting the detection of ADAs (Carrasco-Triguero, M., et al., Bioanalysis, 2012, 4(16): p. 2013-26). Another alternative assay format using human soluble Fcγ receptor I (hsFcγRI) to detect the Fc region of the ADA has also been reported to mitigate soluble target interference, however this format may not be able to detect all potential ADA isotypes (Wessels, U., et al., Bioanalysis, 2016, 8(20): p. 2135-45). A white paper has recently been published describing a number of strategies to mitigate drug target interference in ADA and neutralizing antibody (NAb) assays (Zhong, Z. D., et al., AAPS J, 2017, 19(6): p. 1564-1575). Therefore, it is important to develop reliable test methods that can overcome target interference and provide valid immunogenicity assessments in both nonclinical and clinical studies.

The present invention provides methods for mitigating target interference in ADA immunoassays to reduce false positive results in ADA immunoassays, e.g., bridging immunogenicity assays. In particular, the present disclosure is based, at least in part, on the discovery that the combination of one or more target blocking reagents, e.g., antibodies or target receptor IgG Fc fusion proteins, together with mild basic pH assay conditions, results in high tolerance to recombinant target protein and reduced levels of false positive results in study samples with PK profiles that did not indicate significant ADA response. Accordingly, the methods described herein provide for mitigating target interference where standard acid dissociation procedures and target blocking antibodies alone are ineffective.

I. Definitions

In order that the present invention may be more readily understood, certain terms are first defined. In addition, it should be noted that whenever a value or range of values of a parameter are recited, it is intended that values and ranges intermediate to the recited values are also part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention.

The articles "a" and "an" are used herein to refer to one or to more than one (i.e., to at least one) of the grammatical object of the article. By way of example, "an element" means one element or more than one element.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen" as used herein is meant any substance that causes the immune system to produce antibodies or specific cell-mediated immune responses against it. A disease-associated antigen is any substance that is associated with any disease that causes the immune system to produce antibodies or a specific-cell mediated response against it.

A "binding domain" (also referred to as a "binding region" or "binding moiety"), as used herein, refers to a molecule or portion thereof (e.g., peptide, oligopeptide, polypeptide, protein) that possesses the ability to specifically and non-covalently associate, unite, or combine with a target. A binding domain includes any naturally occurring, synthetic, semi-synthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv), receptor ectodomains, ligands (e.g., cytokines, chemokines), or synthetic polypeptides selected for their specific ability to bind to a biological molecule, a molecular complex or other target of interest.

A "binding molecule" as understood herein is a molecule that specifically interacts with a particular target. Examples of such binding molecules include, but are not limited to, antibodies (including monoclonal antibodies) and fragments thereof, engineered antibodies, fusion proteins, and other like antigen-binding molecules well-known to those skilled in the art. Additionally, the term binding molecule as used herein comprises a receptor or receptor-like molecule that can interact with a target.

"Anti-drug antibodies" or "ADA" are antibodies, which may be directed against any region of the drug, like e.g. the variable domain, the constant domains, or the glycostructure of the drug. Such anti-drug antibodies may occur during antibody therapy as an immunogenic reaction of a patient (see Pan, Y., et al., FASEB J. 9 (1995) 43-49). Most of the "anti-drug antibodies" bind to one or more of the complementary determining regions of the drug. The affinity of anti-drug antibodies to their drug's antigen is in general lower compared to the affinity of the drug for its target antigen.

The term "bridging immunoassay" or "ADA bridging immunoassay" as used herein, denotes a sandwich-type immunoassay in which a bivalent ADA is bound by two different binding molecules (i.e., a capture drug and a detection drug) each binding to a different not overlapping or interfering epitope of the ADA. In this assay, a sandwich comprising the capture antibody, the ADA, and the detection antibody is formed and, thus, the ADA bridges the two antibodies binding to it (see FIG. 1A). The capture antibody can be attached to a solid surface, e.g., a microtiter plate or other solid surface. The bridging immunoassay can be a high-throughput assay. In one aspect, an ADA bridging immunoassay as described herein comprises two antibody drugs, the "capture drug" and the "detection drug." In one embodiment, the detection drug and the capture drug comprise the "same" antibody molecule, e.g., recombinantly produced with the same expression vector and comprising the same amino acid sequence.

pH is a logarithmic scale used to specify the acidity or basicity of an aqueous solution. It is approximately the negative of the base 10 logarithm of the molar concentration, measured in units of moles per liter, of hydrogen ions. More precisely it is the negative of the base 10 logarithm of the activity of the hydrogen ion. Solutions with a pH less than 7 are acidic and solutions with a pH greater than 7 are basic. The term "mild basic pH", as used herein with respect to assay conditions, refers to a pH of between about pH 7.5 to about pH 9.5. In one aspect, a mild basic pH includes a pH of between about pH 8.0 to about pH 9.0. In another aspect, a mild basic pH includes a pH of between about pH 8.5 to about pH 9.5. In another aspect, a mild basic pH includes a pH of between about pH 7.5 to about pH 8.5. In another aspect, a mild basic pH includes a pH of between about pH 7.6, 7.7, 7.8, 7.9, 8.0, 8.1, 8.2, 8.3, or 8.4.

The term "drug", as used herein, refers to a therapeutic protein, or therapeutically effective portion thereof, which can be administered to an individual for the treatment of a disease. In one aspect, the drug is a human therapeutic protein, such as a human therapeutic monoclonal antibody or a human therapeutic fusion protein such as a receptor protein fused to an immunoglobulin Fc domain, e.g., an IgG1 Fc domain. In another aspect, the drug is a humanized therapeutic monoclonal antibody. In another aspect, the drug is a chimeric antibody. In yet another aspect, the drug is a mouse antibody. In one aspect, the therapeutic drug is being evaluated in a clinical trial.

Therapeutic drugs, such as antibody drugs, are being used widely for the treatment of various diseases such as oncological diseases, immunological diseases, central nervous diseases, vascular diseases, and infectious diseases. Antibody drugs that are included in the methods of the invention include any therapeutic antibody approved by a regulatory agency or in clinical or preclinical trials. Antibody drugs that have been approved in the U.S. and EU as of 2018 include, but are not limited to, bezlotoxumab, avelumab, dupilumab, durvalumab, ocrelizumab, brodalumab, reslizumab, olaratumab, daratumumab, elotuzumab, necitumumab, infliximab, obiltoxaximab, atezolizumab, secukinumab, mepolizumab, nivolumab, alirocumab, idarucizumab, evolocumab, dinutuximab, bevacizumab, pembrolizumab, ramucirumab, vedolizumab, siltuximab, alemtuzumab, pertuzumab, infliximab, obinutuzumab, brentuximab, raxibacumab, belimumab, ipilimumab, denosumab, ofatumumab, besilesomab, tocilizumab, canakinumab, golimumab, ustekinumab, certolizumab pegol, catumaxomab, eculizumab, ranibizumab, panitumumab, natalizumab, catumaxomab, bevacizumab, omalizumab, cetuximab, efalizumab, ibritumomab tiuxetan, fanolesomab, adalimumab, tositumomab, alemtuzumab, trastuzumab, gemtuzumab ozogamicin, infliximab, palivizumab, necitumumab, basiliximab, rituximab.

A drug used in the methods of the invention also includes a therapeutic drug that is in development or is undergoing pre-clinical or clinical testing, i.e., being evaluated in a clinical trial.

Antibody drugs can include antibodies targeting any antigen, including, for example, IL-4R, IL-6R, IL-33, PD-1, CD20×CD3, LAG-3, IL-33, Feld 1, C5, ANGPTL-3, ACTIVIN A, GDF8, PCSK9, VEGF, NGF, or a viral antigen, such as ebola or mers-cov.

Additional therapeutic drugs that can be used in the methods of the invention include, for example, evinacumab, trevogrumab, cemiplimab, alirocumab, aflibercept, fasinumab, rilonacept, and sarilumab.

Therapeutic drugs also include biosimilar versions of approved drugs, e.g., antibody or therapeutic fusion proteins. For example, aflibercept biosimilars in development including ALT-L9 (Alteogen), M710 (Momenta/Mylan), FYB203 (Formycon (DE)/Santo Holding GmbH), and CHS-2020 (Coherus).

A "drug target," as used herein, refers to the target of a drug. For example, in one embodiment, the drug target is a dimeric target. In one embodiment, the drug target is a homodimeric drug target. In another embodiment, the drug target is a multimeric drug target. In another embodiment, the drug target is a soluble or shed drug target. A drug target can interfere in an ADA immunoassay and result in false positive assay results.

A "drug target blocking reagent," as used herein, refers to any reagent that is capable of binding to and/or blocking a drug target in an immunoassay, thereby preventing the binding of the drug target to a capture drug or a detection drug. In one embodiment, a drug target blocking reagent is an anti-target blocking antibody. The anti-target blocking antibody can comprise a human constant region or a mouse constant region. In another embodiment, a drug target blocking reagent is a target receptor IgG Fc fusion protein, wherein the fusion protein comprises a portion of a target receptor linked or fused to an IgG Fc domain. In one aspect, the portion of the target receptor is an extracellular portion of the receptor. In a particular aspect, the IgG Fc domain is a human IgG Fc domain. In another aspect, the IgG Fc domain is a mouse IgG Fc domain. As described in detail herein, an ADA immunoassay, e.g., an ADA bridging immunoassay, can comprise one or more drug target blocking reagents which mitigate drug target interference in the immunoassay. For example, in one embodiment, the immunoassay can comprise one drug target blocking reagent. In another embodiment, the immunoassay can comprise two drug target blocking reagents. In one embodiment, both drug target blocking reagents can comprise drug target blocking antibodies. In another embodiment, the assay can comprise one or more drug target blocking antibodies and one or more target receptor IgG Fc fusion proteins.

As used herein, an entity or reagent (e.g., binding molecule, capture drug, detection drug, anti-drug antibody (ADA), drug, protein, enzyme, antibody, antibody fragment, or related species) that is modified by the term "labeled" includes any entity that is conjugated with another molecule or chemical entity that is empirically detectable (e.g., "detectable label"). Chemical species suitable as labels for labeled-entities include, but are not limited to, ruthenium, a radiologic label, a photoluminescent label, a chemiluminescent label, a fluorescent label, an electrochemiluminescent label, an enzyme label, quantum dots, or an optical dye label.

Other labels include, for example biotin, Protein A, Protein G, glutathionin S-transferase (GST). These labels can be used to label capture drug antibodies, which can then be attached to a solid surface.

As used herein, the terms "fluorescent label" and "fluorophore" can be used interchangeably and refer to any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals.

As used here, "target tolerance level" is defined as the amount of target needed to generate a target-mediated false positive signal in the assay (with assay signal above the plate cut point).

The term "sample" includes, but is not limited to, any quantity of a substance from a living thing or formerly living thing. Such living things include, but are not limited to, humans, mice, monkeys, rats, rabbits, and other animals. In one embodiment, such samples include, but are not limited to, whole blood, serum or plasma from a subject. In one embodiment, the sample, e.g., a serum sample, is a sample obtained from a subject during clinical or preclinical testing of a drug. For example, the sample can be obtained from the subject following administration of the drug during a clinical trial.

The term "subject" as used herein refers to a human or non-human organism. Thus, the methods and fusion complexes described herein are applicable to both human and veterinary diseases and conditions. Subjects can be "patients," i.e., living humans or non-human organisms that are receiving medical care for a disease or condition, or humans or non-human organisms with no defined illness who are being investigated for signs of pathology or presence/absence of a particular condition. Subjects also include participants in clinical trials for a drug, wherein the subject has been administered the drug for trial purposes.

The term "Fc domain" or "immunoglobulin Fc" or "Ig Fc" is meant to refer to the immunoglobulin heavy chain "fragment crystallizable" region. Generally, an Fc domain is capable of interacting with a second Fc domain to form a dimeric complex. The Fc domain may be capable of binding cell surface receptors called Fc receptors and/or proteins of the complement system or may be modified to reduce or augment these binding activities. The Fc domain may be derived from IgG, IgA, IgD, IgM or IgE antibody isotypes (referred to herein as an IgG Fc domain, an IgA Fc domain, an IgD Fc domain, an IgM Fc domain, and an IgE Fc domain, respectively). The Fc domain may effect immune activity including opsonization, cell lysis, degranulation of mast cells, basophils, and eosinophils, and other Fc receptor-dependent processes; activation of the complement pathway; and protein stability in vivo.

The term "polypeptide" is meant to refer to any polymer comprising any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted. Peptides useful in accordance with the present disclosure in general will be generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis.

The term "soluble" as used herein is meant that a fusion molecule is soluble if it remains in aqueous solution at a temperature greater than about 5-37° C. and at or near neutral pH in the presence of low or no concentration of an anionic or non-ionic detergent. Under these conditions, a soluble protein will often have a low sedimentation value, e.g., less than about 10 to 50 Svedberg units. Aqueous solutions referenced herein typically have a buffering compound to establish pH, typically within a pH range of about 5-9, and an ionic strength range between about 2 mM and 500 mM. Sometimes a protease inhibitor or mild non-ionic detergent is added. Additionally, a carrier protein may be added if desired such as bovine serum albumin (BSA) to a few mg/mL. Exemplary aqueous buffers include standard phosphate buffered saline, tris-buffered saline, or other well-known buffers and cell media formulations.

The term "solid surface" means a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; cuvettes, tubes, or other spectrometer sample containers.

The term "isolated" refers to a composition, compound, substance, or molecule altered by the hand of man from the natural state. For example, a composition or substance that occurs in nature is isolated if it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein.

II. Mitigating Target Interference

The ADA bridging immunoassay for detecting ADA in a sample, as described in detail below, is susceptible to drug target interference (false positive ADA). In an ADA bridging immunoassay, a sample is incubated with a capture drug (labeled or unlabeled), and a detection drug, comprising a detectable label. After sample incubation, a sandwich comprising a capture drug, the ADA, and a detection drug is formed and, thus, the ADA bridges two drugs binding to it and the bound ADA can be detected (see FIG. 1A). A true positive signal in the ADA bridging assay results from bivalent binding of the ADA to the capture drug and the detection drug, forming a bridge. However, a false-positive result arises when a dimeric or multimeric target bridges the capture drug and the detection drug, thereby forming a bridge with the target (see FIG. 1B and, e.g., Liao, K., et al., J Immunol Methods, 2017, 441: p. 15-23).

As demonstrated in the Example provided herein, the present invention provides methods for mitigating drug target interference in an ADA bridging immunoassay, thereby reducing false positive results. The methods comprise incubating a sample with at least one drug target blocking reagent at mild basic pH assay conditions.

In one embodiment, the invention provides a method for mitigating drug target interference in an ADA bridging immunoassay for the determination of the presence of an ADA against a drug in a serum sample. This method comprises contacting the serum sample with a capture drug, a detection drug, and one or more drug target blocking reagents. Next, these components are incubated under mild basic pH assay conditions allowing the drug target blocking reagent to interact with the drug target present in the sample, thereby mitigating the interference of the drug target in the ADA bridging immunoassay.

In one aspect, the method further comprises performing the ADA bridging immunoassay, as described below.

In another aspect, the one or more drug target blocking reagent is capable of binding to and/or blocking a drug target in an immunoassay, thus preventing the binding of the drug target to a capture drug and/or a detection drug. In a particular aspect, the one or more drug target blocking reagent is a target blocking binding molecule such as an antibody. In a still further aspect, the target blocking antibody comprises a human constant region.

Where the target blocking binding molecule (e.g., an antibody) and the drug (e.g., an antibody drug) have the same human constant regions, ADA in the serum samples that are specific to the Fc region of the drug may bind to the target blocking human antibody and potentially compromise detection in the assay. Replacement of the human Ig regions of the target blocking antibody with mouse Ig regions can result in a reduction in interference of the drug target blocking antibody with ADA detection. Thus, in one aspect, the target blocking antibody comprises a mouse constant region.

The ADA bridging immunoassay can comprise one or more drug target blocking reagents. In one aspect, the immunoassay comprises two drug target blocking reagents. In a particular aspect, the two drug target blocking reagents are drug target blocking antibodies, e.g., a first drug target blocking antibody and a second drug target blocking antibody. In a more particular aspect, the first and/or the second target blocking antibodies comprise human constant regions. In another particular aspect, the first and/or the second target blocking antibodies comprise mouse constant regions. In still another aspect, both the first and the second target blocking antibodies comprise human constant regions. In yet another aspect, both the first and the second target blocking antibodies comprise mouse constant regions. In another aspect, the first target blocking antibody comprises a human constant region and the second target blocking antibody comprises a mouse constant region. In yet another aspect, the first target blocking antibody comprises a mouse constant region and the second target blocking antibody comprises a human constant region.

In one embodiment, the invention provides methods for mitigating drug target interference in an ADA bridging immunoassay for the determination of the presence of an ADA against a drug in a serum sample, comprising contacting the serum sample with a capture drug, a detection drug, a first drug target blocking antibody, and a second drug target blocking antibody. These components are incubated under mild basic pH assay conditions thus allowing the first drug target blocking antibody and the second drug target blocking antibody to interact with the drug target present in the sample, thereby mitigating the interference of the drug target in the ADA bridging immunoassay.

As described herein, it was found by the inventors that the target blocking antibodies used in the ADA bridging immunoassay may share some common CDR VH rearrangements with the drug being tested. Accordingly, ADAs specific to these VH rearrangement regions may bind to the target blocking antibody in the sample, potentially compromising their detection in the assay. In order to optimize detection, a target receptor fused to a human IgG Fc was engineered and used in the methods of the invention in place of one of the target blocking antibodies.

In one embodiment, one or more of the drug target blocking reagents used in the methods of the invention comprises a portion of a target receptor fused to an IgG Fc domain (a target receptor IgG Fc fusion protein). In one aspect, the portion of the target receptor is an extracellular portion of the receptor. In another aspect, the target receptor IgG Fc fusion protein is soluble. In a particular aspect, the IgG Fc domain of the target receptor IgG Fc fusion protein is a human IgG Fc domain.

Where the target receptor IgG Fc fusion protein and the drug have human IgG Fc regions, ADA in the serum samples that are specific to the Fc region of the drug may bind to the target receptor IgG Fc fusion protein and potentially compromise detection in the assay. Replacement of the human Ig Fc regions of the target receptor IgG Fc fusion protein with mouse Ig regions may result in a reduction in interference of the target receptor IgG Fc fusion protein with ADA detection. Therefore, in another aspect, the IgG Fc domain of the target receptor IgG Fc fusion protein is a mouse IgG Fc domain.

The assay may comprise one or more drug target blocking antibodies and one or more target receptor IgG Fc fusion proteins. Further, the assay may comprise a target blocking antibody and a target receptor IgG Fc fusion protein.

Accordingly, in one embodiment, the invention provides a method for mitigating drug target interference in an ADA bridging immunoassay for the determination of the presence of an ADA against a drug in a serum sample, wherein the drug target is a soluble protein such as, e.g., a ligand to a receptor and the method comprises contacting the serum sample with a capture drug, a detection drug, a drug target blocking reagent comprising an extracellular portion of the receptor fused to an IgG Fc domain, and a drug target blocking antibody. These components are incubated under mild basic pH assay conditions allowing the drug target blocking reagent and the drug target blocking antibody to interact with the drug target present in the sample, thereby mitigating the interference of the drug target in the ADA bridging immunoassay.

In one aspect, the IgG Fc domain is a mouse IgG Fc domain. In another aspect, the IgG Fc domain is a human IgG Fc domain. In yet another aspect, the drug target blocking antibody comprises a human constant region. In still another aspect, the drug target blocking antibody comprises a mouse constant region. In one aspect, the target receptor IgG Fc fusion protein comprises a mouse IgG Fc and the target blocking antibody comprises a mouse constant region.

In one embodiment, the target blocking reagents each have a concentration in the ADA bridging immunoassay of about 10 µg/mL to about 200 µg/mL. In one aspect, the target blocking reagents each have a concentration of about 20 µg/mL to about 175 µg/mL. In another aspect, the target blocking reagents each have a concentration of about 30 µg/mL to about 150 µg/mL. In still another aspect, the target blocking reagents each have a concentration of about 40 µg/mL to about 125 µg/mL. In yet another aspect, the target blocking reagents each have a concentration of about 50 µg/mL to about 100 µg/mL. In another aspect, the target blocking reagents each have a concentration of about 50, 60, 70, 75, 80, 85, 90, 95, or 100 µg/mL. In another aspect, the target blocking reagents each have a concentration of about 100 µg/mL.

The methods for mitigating target interference described herein comprise performing the ADA immunoassay under mild basic pH assay conditions. The mild basic pH includes a range of pH values slightly above neutral pH. In one embodiment, a mild basic pH refers to a pH of between about pH 7.5 to about pH 9.5. In one aspect, a mild basic pH includes a pH of between about pH 7.5 to about pH 8.5. In one aspect, a mild basic pH includes a pH of between about pH 8.5 to about pH 9.0. In one aspect, a mild basic pH includes a pH of between about pH 8.0 to about pH 9.0. In another aspect, a mild basic pH includes a pH of between about pH 8.5 to about pH 9.5.

III. ADA Immunoassays

Immunoassays are well known to the skilled artisan. Methods for carrying out such assays as well as practical applications and procedures are well-known in the art and described in, for example, Colowick, S. P. and Caplan, N. O. (eds.), "Methods in Enzymology", Academic Press, dealing with immunological detection methods, especially volumes 70, 73, 74, 84, 92, and 121. The principles of different immunoassays are described, for example, by Hage, D. S. (Anal. Chem. 71 (1999) 294R-304R). Lu, B., et al. (Analyst 121 (1996) 29R-32R) which describes the orientated immobilization of antibodies for the use in immunoassays. Avidin-biotin-mediated immunoassays are described, for example, by Wilchek, M., and Bayer, E. A., in Methods Enzymol. 184 (1990) 467-469.

A commonly used ADA assay method is a bridging immunoassay (see, e.g., Liao, K., et al., J Immunol Methods, 2017, 441: p. 15-23; Dai, S., et al., AAPS J, 2014, 16(3): p. 464-77; and Zhong, Z. D., et al., AAPS J, 2017. 19(6): p. 1564-1575, the contents of which are incorporated by reference herein). An ADA bridging immunoassay is a sandwich-type immunoassay in which a multi-valent ADA is bound by two different antibody drugs (a capture drug and a detection drug), each binding to a different not overlapping or interfering epitope of the ADA. In particular, in this assay, a sample is incubated with a capture drug (labeled or unlabeled), and a detection drug, comprising a detectable label. After sample incubation, a sandwich comprising a capture drug, the ADA, and a detection drug is formed and, thus, the ADA bridges two drugs binding to it and the bound ADA can be detected (see FIG. 1A). In one aspect, the immunoassay is a high-throughput assay.

The ADA bridging immunoassay further comprises determining the presence of or amount of an ADA. Thus, the present disclosure provides a detection drug conjugated to a detectable label. Non-limiting examples of detectable labels for any of the methods of the invention include ruthenium, a radiologic label, a photoluminescent label, a chemiluminescent label, a fluorescent label, a fluorophore, a hapten, an electrochemiluminescent label, or an enzyme label. The detectable label can be measured using instruments and devices known to those skilled in the art.

Representative fluorophores for use in the methods provided herein include, e.g., green fluorescent protein, blue fluorescent protein, red fluorescent protein, fluorescein, fluorescein 5-isothiocyanate (FITC), cyanine dyes (Cy3, Cy3.5, Cy5, Cy5.5, Cy7), Bodipy dyes (Invitrogen) and/or Alexa Fluor dyes (Invitrogen), dansyl, Dansyl Chloride (DNS-C1), 5-(iodoacetamida)fluorescein (5-IAF, 6-acryloyl-2-dimethylaminonaphthalene (acrylodan), 7-nitrobenzo-2-oxa-1,3-diazol-4-yl chloride (NBD-Cl), ethidium bromide, Lucifer Yellow, rhodamine dyes (5-carboxyrhodamine 6G hydrochloride, Lissamine rhodamine B sulfonyl chloride, rhodamine-B-isothiocyanate (RITC (rhodamine-B-isothiocyanate), rhodamine 800); tetramethylrhodamine 5-(and 6-) isothiocyanate (TRITC)), Texas Red, sulfonyl chloride, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, Naphtyl Styryl, 3,3'dipropylthiadicarbocyanine (diS-C3-(5)), 4-(p-dipentyl amino styryl)-1-methylpyridinium (di-5-ASP), Cy-3 Iodo Acetamide, Cy-5-N-Hydroxysuccinimide, Cy-7-Isothiocyanate, IR-125, Thiazole Orange, Azure B, Nile Blue, Al Phthalocyanine, Oxaxine 1,4',6-diamidino-2-phenylindole. (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Haptens for use in the methods provided herein include, e.g., digoxigenin, and biotin.

Enzymes for use in the methods provided herein include, for example, alkaline phosphatase (AP), β-galactosidase, horse radish peroxidase (HRP), soy bean peroxidase (SBP), urease, β-lactamase and glucose oxidase.

In one embodiment, the capture drug is conjugated to a solid surface. In one aspect, the conjugation of the capture drug to the solid surface is performed via a specific binding pair, wherein the capture drug is labeled or conjugated. In one aspect, the specific binding pair (first component/second component) is selected from streptavidin or avidin/biotin, biotin/neutravidin, biotin/captavidin, antibody/antigen (see, e.g., Hermanson, G. T., et al., Bioconjugate Techniques, Academic Press, 1996), epitope/antibody, protein A/immunoglobulin, protein G/immunoglobulin, protein L/immunoglobulin, GST/glutathione, His-tag/Nickel, FLAG/M1 antibody, maltose binding protein/maltose, calmodulin binding protein/calmodulin, enzyme/enzyme substrate, lectin/polysaccharide, steroid/steroid binding protein, hormone/hormone receptor, and receptor-ligand binding pairs. In one aspect, the capture drug is conjugated to biotin (as first component of a specific binding pair). In this case the conjugation to the solid phase is performed via immobilized avidin or Streptavidin (see FIG. 1A).

In some embodiments, a GlcNac binding protein is conjugated to a first member of binding pair (e.g., biotin, avidin, neutravidn, captavid, antibody, antigen, protein A, protein G, protein L, GST, His-Tag, FLAG, MBP, calmodulin binding protein, an enzyme, a receptor or ligand).

In one embodiment, the sample being tested in the ADA immunoassay is a serum sample. In one aspect, the serum sample comprises 1% to 20% serum. In one aspect, the serum sample comprises from about 1% to about 10% serum. In another aspect, the serum sample comprises from about 10% to about 15% serum. In yet another embodiment, the serum sample comprises from about 10% to about 20% serum. In still another embodiment, the serum sample comprises from about 15% to about 20% serum. In a particular aspect, the serum sample comprises about 1% serum. In one aspect the serum is human serum.

In one embodiment, the ADA bridging immunoassay comprises an acid-dissociation step. In one aspect, the serum sample is diluted 10-fold in acid, e.g., acetic acid, and incubated at room temperature prior to incubation with the capture drug and the detection drug.

In one embodiment, the capture drug and the detection drug have a concentration in the immunoassay of about 0.5 µg/mL to about 10 µg/mL. In one aspect, the capture drug and the detection drug have a concentration of more than 0.5 µg/mL to less than 10 µg/mL. In another aspect, the capture drug and the detection drug have a concentration of about 0.5 µg/mL to about 5 µg/mL. In yet another aspect, the capture drug and the detection drug have a concentration of about 0.5 µg/mL to about 2.0 µg/mL. In still another aspect, the capture drug and the detection drug have a concentration of about 0.5 µg/mL to about 1 µg/mL. In a preferred aspect, the capture drug and the detection drug have a concentration of about 0.5 µg/mL.

In one embodiment, incubation of the sample, the capture drug and the detection drug is carried out at room temperature. In one aspect, the incubation time of the sample, the capture drug and the detection drug is at least 0.5 hours. In another aspect, the incubation time is at least 1 hours. In one aspect the incubation time is at least 1.5 hours. In one aspect, the incubation time is up to 2 hours. In still another aspect, the incubation time is between 0.5 hours and 12 hours. In one aspect, the incubation time is between 0.5 hours and 5 hours. In another aspect, the incubation time is between 1 hours and 12 hours. In one aspect, the incubation time is between 1 hour and 5 hours. In another aspect, the incubation time is between 5 and 12 hours.

In one embodiment, following incubation of the of the sample, the capture drug and the detection drug, the sample is transferred to a labeled solid surface, e.g., a streptavidin labeled solid surface, and incubated further, so that the capture drug can attach to the solid surface. In one aspect, incubation is at room temperature. In another aspect, following incubation the samples are analyzed for binding to an ADA using any method known in the art for detection of labeled antibodies, wherein the detection drug is detected based on detection of the drug label, e.g., ruthenium. A true positive signal in the ADA bridging assay results from bivalent binding of the ADA to the capture drug and the detection drug, forming a bridge.

Solid surfaces for the immunoassays described herein are widely described in the state of the art (see, e.g., Butler, J. E., Methods 22 (2000) 4-23, which is incorporated herein by reference). A solid surface component of an assay is distinguished from inert solid surfaces with which the assay may be in contact in that a "solid surface" contains at least one moiety on its surface, which is intended to interact with the capture drug. A solid surface may be a stationary component, such as a tube, strip, cuvette, or microtiter plate, or may be a non-stationary component, such as beads and microparticles. Microparticles can also be used as a solid phase for homogeneous surface formats. A variety of microparticles that allow either non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See, e.g., Martin, C. R., et al., Analytical Chemistry-News & Features 70 (1998) 322A-327A, which is incorporated herein by reference.

The present invention is further illustrated by the following Examples, which is not intended to be limiting in any way. The entire contents of all references, patents and published patent applications cited throughout this application, as well as the Figures, are hereby incorporated herein by reference.

EXAMPLES

Example 1: Mitigating Target Interference in Bridging Immunogenicity Assay with Target Blocking Reagents and Mild Basic pH Materials and Methods Materials and Reagents For the functional drug assay and the target assay described herein, all solutions, unless otherwise specified, were prepared in assay buffer (0.5% BSA, 0.05% Tween-20, 1×PBS). For the ADA assay described herein, all solutions, unless otherwise specified, were prepared in 1% BSA, 1×PBS. PBS was from Life Technologies (Grand Island, NY). 1.5 M Trizma base was from Sigma (St Louis, MO). Glacial acetic acid was from Thermo Fisher Scientific (Waltham, MA). HBS-EP+ (10×) buffer was from GE Life Science (Marlborough, MA). Human serum was from Bioreclamation (Hicksville, NY). Streptavidin-coated microplates were from Meso Scale Discovery (Rockville, Maryland). Recombinant human target protein was from R&D System (Minneapolis, MN). Black microwell plates, Horseradish Peroxidase (HRP)-conjugated NeutrAvidin™ and SuperSignal ELISA Pico Chemiluminescent Substrate™ were from Thermo Fisher Scientific (Rockford, IL). HRP-conjugated goat anti-mouse IgG, Fc fragment specific, antibody was from Jackson ImmunoResearch (West Grove, PA). The AHC biosensors (Anti human IgG Fc Capture) were from Pall ForteBio (Fremont, CA). Fully human monoclonal antibody drug, mouse anti-drug monoclonal antibody, biotinylated drug, ruthenylated drug, and all human and mouse anti-target monoclonal antibodies (referred to herein as HuAb1, HuAb2 (human) and MsAb2 (mouse)), soluble human and mouse receptor fusion proteins (referred to herein as HuSR and MsSR, respectively), and the biotinylated human anti-target monoclonal antibody (used in the ADA and target assay) were produced by Regeneron Pharmaceuticals (Tarrytown, NY).

pH Determination pH measurements were performed using a calibrated Mettler Toledo meter (Columbus, Ohio) with an InLab Expert Pro-ISM™ electrode. Pooled human serum was diluted 10-fold in 300 mM acetic acid. The acidified samples were then buffered 10-fold with different concentrations of Tris-base solutions. pH measurements were performed on the final assay solutions as shown in Table 1, below.

TABLE 1

| pH Conditions Evaluated for Detection of Anti-Drug ADA | |
|---|---|
| Solution Pooled human serum 1:10 in 300 mM acetic acid, then 1:10 in Master Mix | pH |
| 70 mM Tris | 8.43 |
| 60 mM Tris | 8.30 |
| 50 mM Tris | 8.13 |
| 40 mM Tris | 7.83 |

ADA Assay

Anti-drug antibodies (ADA) in human serum samples were detected using a non-quantitative ADA bridging immunoassay (FIGS. 1A-C). This ADA bridging assay employs a mouse anti-drug monoclonal antibody as the positive control and biotinylated drug and ruthenylated drug as the bridge components (FIG. 1A). Serum samples were acidified by diluting them 10-fold in 300 mM acetic acid and incubated at room temperature (RT) for at least 10 minutes. Biotinylated drug and ruthenylated drug (0.5 µg/mL) were prepared in assay buffer containing 60 mM Tris-base prior to addition to serum samples. Acid-treated serum samples were then diluted 10-fold in the labeled drug solution. After incubation for about 60 minutes at room temperature, samples were transferred to blocked (5% BSA) Streptavidin Multi-Array™ 96-well plates (MSD) and incubated for about 60 minutes at room temperature. The plate was washed and Read Buffer was added and the plates were read using a MSD plate reader such as, e.g., SECTOR Imager 2400. To block target-mediated interference (FIG. 1B), an anti-target monoclonal antibody (100 m/mL) and/or a soluble receptor protein (100 m/mL) were also included in the labeled drug solution (FIG. 1C). Furthermore, the labeled drug solution was prepared in 60 mM Tris to adjust the pH to a mild basic condition, which also minimizes the binding of target to both biotinylated drug and ruthenylated drug.

Target Assay

The procedure employs a microtiter plate coated with a mouse anti-target monoclonal antibody (1 m/mL), and utilizes recombinant target protein as a standard. Standards and QCs were prepared in medium well known to those skilled in the art, to avoid interference by endogenous target protein from human serum. Standards, controls, and samples were diluted 10-fold in 300 mM acetic acid and incubated at room temperature for about 30 minutes. The acid treated samples were neutralized (1:2 dilution) using a 300 mM Tris-base solution spiked with an anti-drug monoclonal antibody (100 m/mL), to minimize the drug interference, prior to addition to the plate. Target protein captured on the plate was detected using a different biotinylated human anti-target monoclonal antibody (200 ng/mL) followed by NeutrAvidin™ conjugated to horseradish peroxidase (NeutrAvidin-HRP™) (100 ng/mL). A luminol-based substrate specific for peroxidase was added to achieve a signal intensity that is proportional to the concentration of total target.

Functional Drug Assay

The functional drug assay quantitates the level of antibody drug that is either unbound to target or has only one arm bound to target. As such, it is still able to bind to the target molecule. The procedure employed a microtiter plate coated with the target (0.5 µg/mL) and utilized the antibody drug as the standard. Drug captured on the plate was detected using a mouse anti-human IgG4 monoclonal antibody (250 ng/mL), followed by horseradish peroxidase conjugated goat anti-mouse IgG, Fc specific (anti-mouse IgG-HRP) (100 ng/mL). A luminol-based substrate specific for peroxidase was then added to achieve a signal intensity that is proportional to the concentration of functional drug.

Biolayer Interferometry

Target binding to antibody drug in the absence and presence of mouse target blocking antibody MsAb2 and soluble mouse receptor fusion protein MsSR under pH 7.3 or 8.3 was studied on an Octet RED96 system (Pall Forte Bio) at 30° C. with a shake speed of 1000 rpm. The AHC biosensors were pre-equilibrated with a dilution buffer containing 10 mM HEPES, 150 mM NaCl, 3 mM EDTA, 0.02% (v/v) Sodium Azide, 1 mg/mL BSA, pH 7.3 for 30 minutes.

The loading step was performed with a drug concentration of 5 µg/mL in the same dilution buffer for 20 seconds (to achieve a thickness of ~0.5 nm) followed by a 60 second baseline step in the same dilution buffer before the biosensors were submerged into the wells containing 200 µL of the target at a concentration of 60 nM with or without 60 nM of MsAb2 and MsSR at pH 7.3. The same procedure was also performed under a pH 8.3 environment. The association curves were collected for a total of ~200 seconds followed by a ~300 second dissociation phase.

Results and Discussion

Mild Basic pH Assay Conditions with Target Blocking Antibody HuAb1 Increase the Target Tolerance Levels and Reduce the Background Signals in Human Naïve Samples Reported target levels in normal human serum are about 10 ng/mL. Target forms complexes with antibody drug and several inhibitory binding proteins in circulation. Anti-drug antibodies were measured with a bridging ADA immunogenicity assay employing an acid-dissociation step (FIGS. 1A-C). While acid treatment usually increases drug tolerance levels, it releases the target complexed with drug and any target binding proteins, resulting in high background signals in naïve human serum sample (FIG. 2A) Similar findings have been previously reported when acid pretreatment was used to dissociate ADA and fulranumab. NGF-fulranumab complexes also dissociated to release free NGF, which interfered in the ADA assay and produced false-positive results (Dai, S., et al., AAPS J, 2014, 16(3): p. 464-77).

Figure 2B:
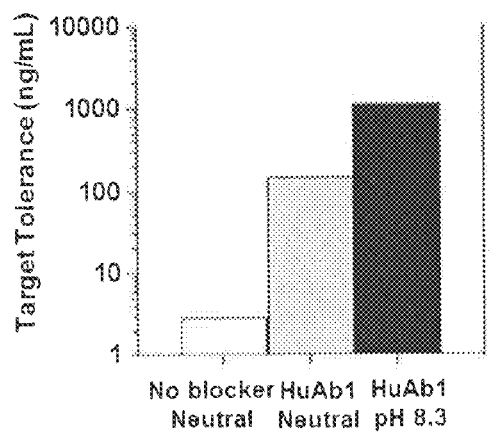
Figure 2C:
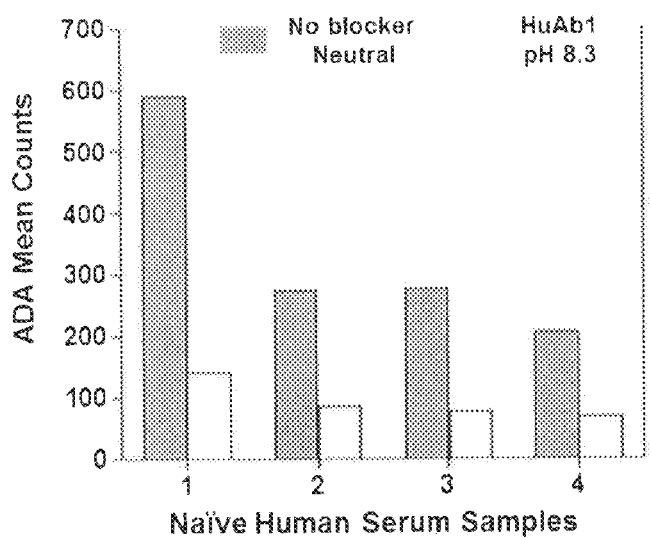

In the ADA assay, without the target blocking antibody and under neutral assay pH, the target tolerance level (defined as the amount of target needed to obtain an assay signal above the plate cut point), determined using a recombinant target protein, is about 3 ng/mL (FIG. 2B). The target tolerance level increases to about 150 ng/mL in the presence of 100 µg/mL of the target blocking antibody HuAb1 at neutral assay pH. Interestingly, with assay pH 8.3 and the same concentration of human target blocking antibody HuAb1, the target tolerance level increased to about 1.1 µg/mL (FIG. 2B). The target tolerance level is even higher, about 7.5 µg/mL, when the assay pH is 8.9. Sensitivity and the drug tolerance limit (DTL) values of the assay were similar under either neutral pH or pH 8.3. The assay signal in naïve human serum samples was also reduced to background level with 100 µg/mL of HuAb1 and with mild basic pH (FIG. 2C).

Figure 3A:
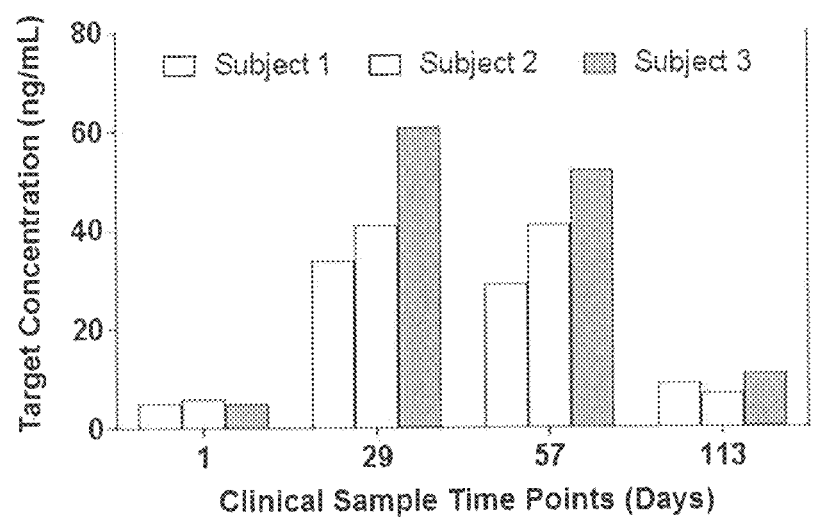
FIGS. 3A-D depict that ADA signal obtained from the analysis of clinical study samples from different subjects, using the target blocking antibody HuAb1 and assay pH 8.3 correlated with target levels but were inconsistent with their pharmacokinetic profiles.
Figure 3B:
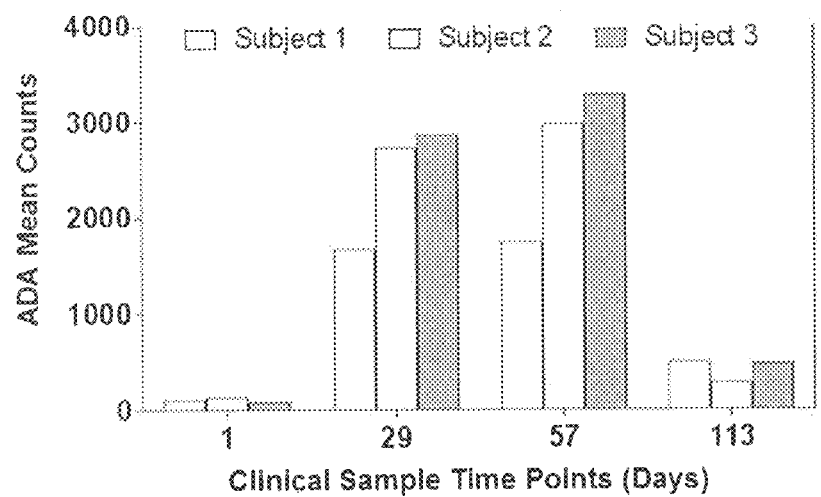

Mild Basic pH in Combination with Two Target Blocking Reagents Inhibit Target Mediated Background Signals in Clinical Study Samples To test whether the combination of human target blocking antibody HuAb1 and mild basic pH conditions could also inhibit target interference in clinical study samples, Phase I clinical samples from three subjects, from a single dose study with drug, at 4 different time points (Days 1, 29, 57 and 113), were tested. In Day 29 and Day 57 samples, a 10 to 12-fold increase in target levels was observed (FIG. 3A), with target levels close to baseline in Day 113 samples, as measured with an in-house target assay. The highest target concentration observed in these samples was about 60 ng/mL, much lower than the target tolerance level of the ADA assay. However, when these samples were tested in the ADA assay, with 100 µg/mL human target blocking antibody HuAb1 at pH 8.3, positive signals were detected in Day 29 and Day 57 samples, with assay signals close to the background levels in Day 113 samples (FIG. 3B).

Figure 3C:
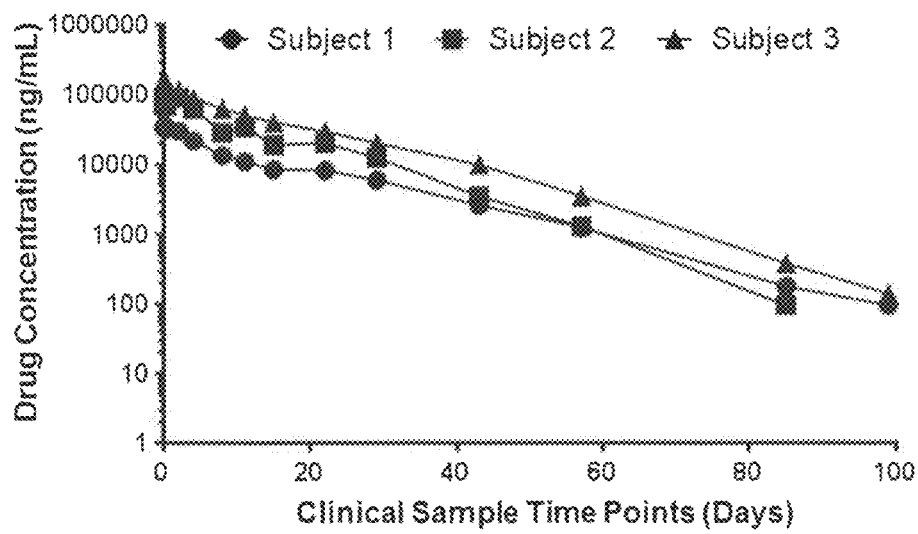

These subjects received a single dose of antibody drug and their PK profiles did not suggest a significant ADA response (FIG. 3C). In addition, the ADA signals in these samples appear to correlate with their target levels. Subsequently, a large group of post-dose samples were also tested, with the majority showing positive ADA signals. Therefore, it is likely that the presence of elevated target levels is responsible for the positive signal in the assay, by creating a target-mediated bridge with the labeled drugs.

Figure 3D:
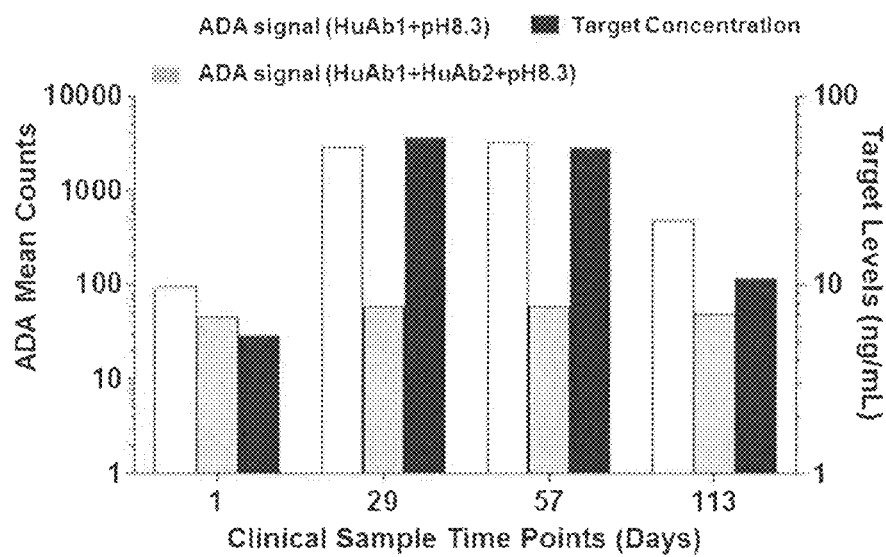

To further mitigate the apparent target interference observed in these clinical samples, a second human target blocking antibody HuAb2 was added to HuAb1 in combination with either neutral pH or mild basic pH. Interestingly, the target mediated background signal decreased significantly with 100 μg/mL of target blocking antibodies HuAb1 and HuAb2 with the neutral assay pH, although not to baseline levels. However, a subset of post-dose samples still generated assay signals above the plate cut point. When these samples were examined again with the same concentration of target blocking antibodies HuAb1 and HuAb2, but with assay pH 8.3, they all had assay signals below the plate cut point (FIG. 3D).

The original assay format with the basic pH and with 100 μg/mL target blocking antibody HuAb1 appeared to be able to tolerate about 1.1 μg/mL recombinant target protein (FIG. 2A). However, in clinical samples, which had relatively low target protein levels (<60 ng/mL) target interference was observed. This indicates that the recombinant target protein may not behave in the assay similarly to the native protein and/or that different forms of the target protein may be expressed in patients, with different binding properties when compared to the recombinant protein, making the target blocking antibody HuAb1 less effective in inhibiting target interference in clinical samples. This discrepant result in the ADA assay between the recombinant and the endogenous target protein highlights the importance of using actual study samples to characterize assay performance.

Another interesting finding was the impact of mild basic pH on target tolerance levels. The combination of HuAb1 and HuAb2 did not completely inhibit the target interference in these clinical samples under neutral pH conditions. Slightly basic conditions along with the two target blocking antibodies were required to completely eliminate the target interference.

Figure 4A:
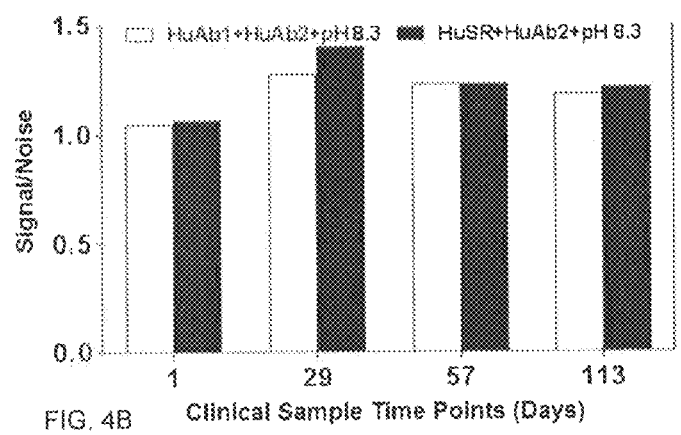
FIGS. 4A-C depict the signal to noise ratio (assay signal of the sample compared to the assay background signal) after further assay optimization to not only inhibit the target interference but also avoid the possible false negative signals.

The Combination of Target Receptor MsSR and Target Blocking Antibody MsAb2 Also Mitigates Target Interference Target blocking antibody HuAb1 shares some common CDR VH re-arrangements with the therapeutic antibody drug, therefore, any ADA specific to these VH re-arrangement regions may bind to HuAb1 in the assay buffer, rather than to the labeled drugs, potentially compromising their detection in the assay. To overcome this potential problem, HuSR, which is a target receptor with a human IgG Fc-fusion, was initially used to replace target blocking antibody HuAb1. As shown in FIG. 4A, the combination of 100 μg/mL of HuAb2 and 100 μg/mL of HuSR can effectively inhibit the target mediated background signals in the phase I clinical samples. In fact, similar target tolerance levels were obtained with either the HuAb2/HuSR or the HuAb1/HuAb2 combination.

Figure 4B:
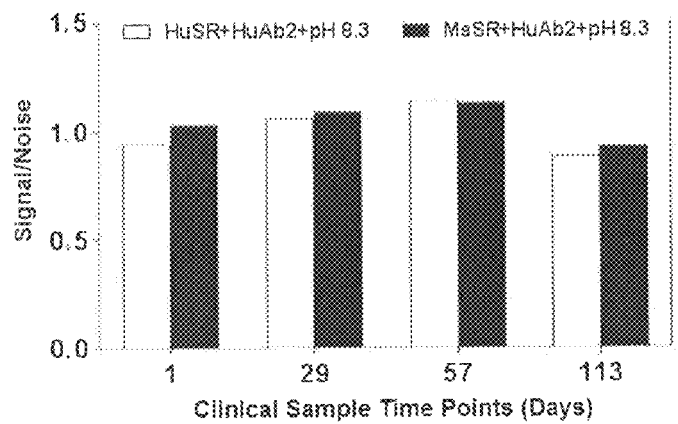
Figure 4C:
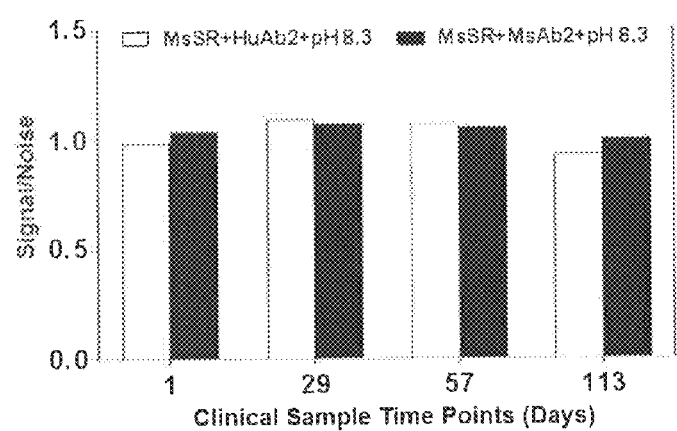
Figure 5:
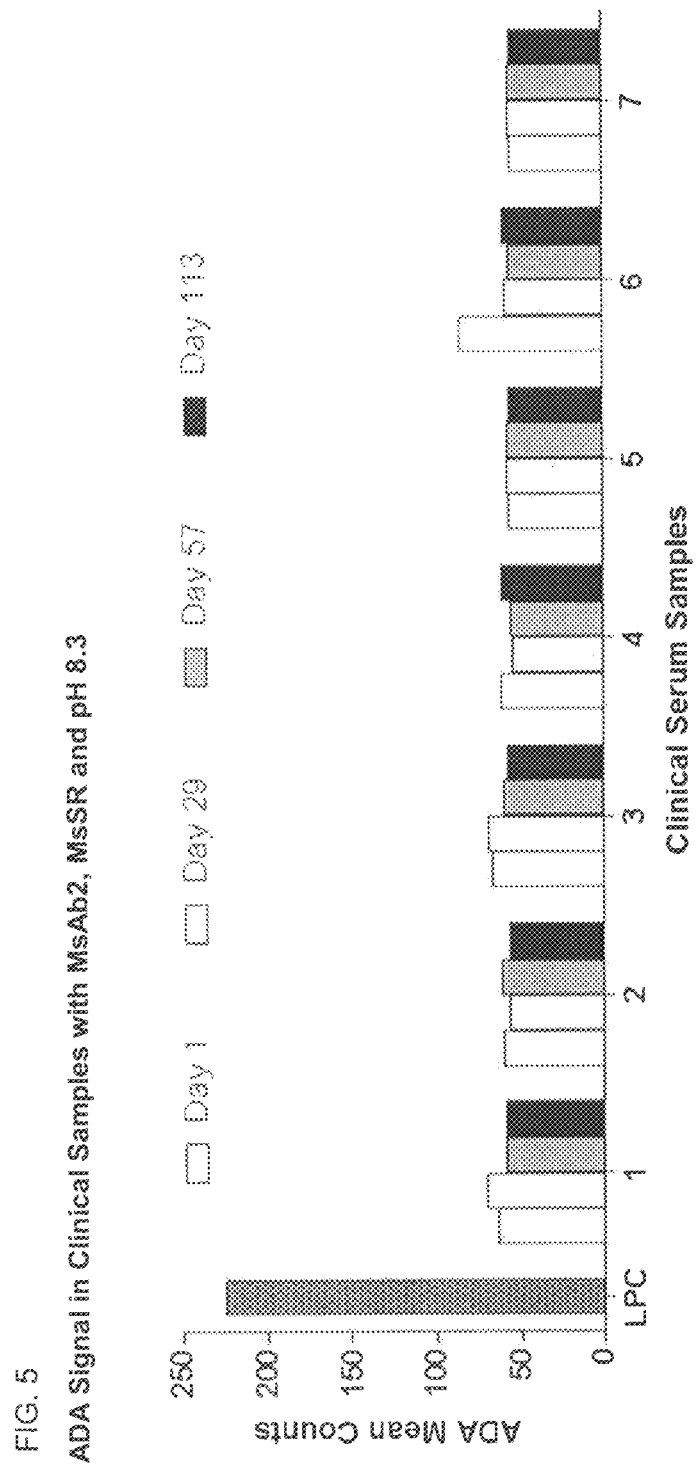
FIG. 5 depicts elimination of target interference in clinical study samples with 100 µg/mL of MsSR, 100 µg/mL of MsAb2 and assay pH 8.3. Only background assay signal was detected in clinical study samples from 7 subjects at 4 different time points (Day 1, 29, 57 and 113).

In addition, the target blocking antibody HuAb2 has the same human IgG4 constant region as the antibody drug and the target receptor HuSR has a human IgG Fc. Any anti-drug antibodies in patient serum samples specific to the Fc region of antibody drug may bind to HuAb2 and HuSR, which may also potentially compromise their detection in the assay. In order to overcome this potential problem, the Fc domain of HuSR and the entire constant region of HuAb2 were converted from human to mouse to further reduce their possible interference in ADA detection. The combination of MsAb2 (HuAb2 with mouse constant region) and MsSR (HuSR with mouse Fc) still effectively mitigated target interference in clinical samples (FIG. 4B and FIG. 4C). Day 1, 29, 57 and 113 clinical samples exhibited only background signals with this new assay format, even though they had high levels of target present in the serum (FIG. 5).

Mild Basic pH and Target Blocking Reagents have Minimal Impact on Real ADA Detection in Rabbit Bleeds and in Rat Toxicology Samples In order to ensure the mild basic pH and the target blocking reagents have minimal impact on the stability and/or the detection of ADA, early bleeds from drug Fab-immunized rabbits were analyzed with the current assay format.

Bleed 1 and bleed 2 from two rabbits collected about 30 to 40 days after immunization were assayed with the two target blocking reagents at either neutral pH or at pH 8.3. These early rabbit bleeds usually have polyclonal antibody responses to the drug with low affinities, whose detection might be more impacted by more stringent assay conditions. As shown in FIG. 6A, the ADA Mean Count values were similar under each assay condition regardless of the assay pH, indicating that the mild basic pH and the addition of target blocking reagents had minimal to no impact on the stability or the detection of the ADA in these samples.

Figure 6B:
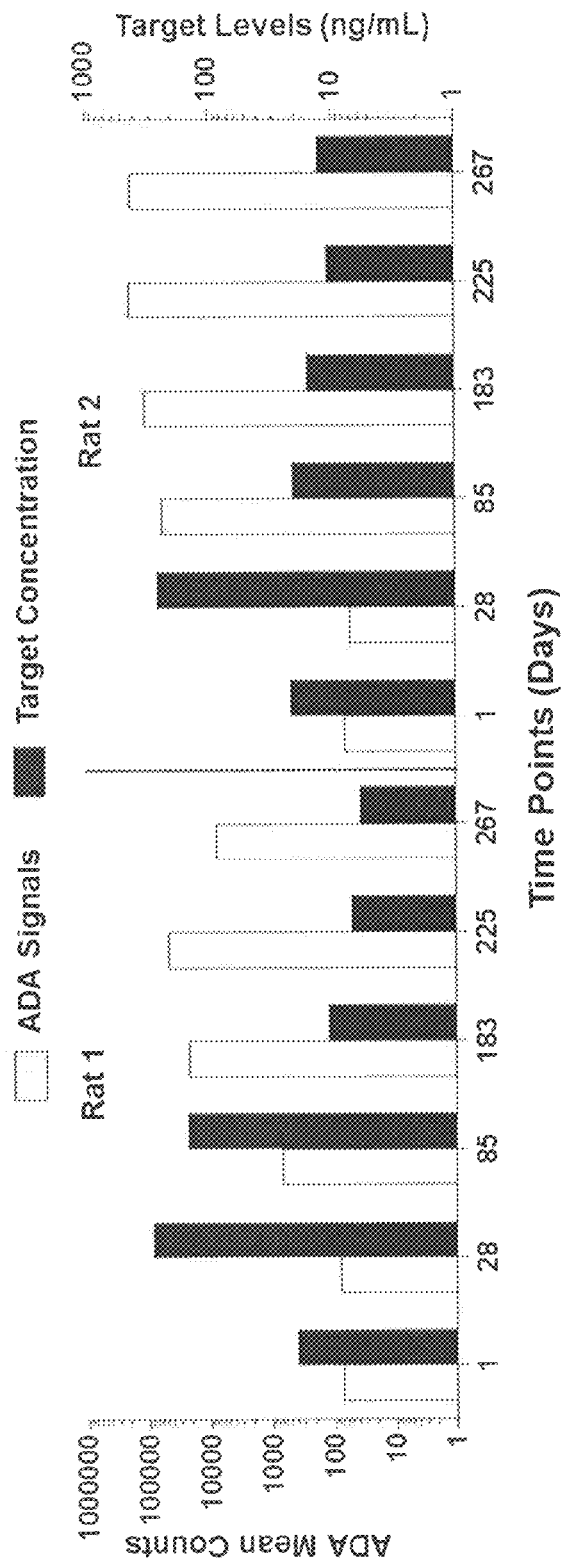

To further confirm that the format using two target blocking reagents at pH 8.3 can detect ADA in post-dose samples, rat serum samples from 2 rats in a toxicology study were analyzed for both target and ADA levels. Target levels increased at least by 10-fold in the Day 28 and 85 samples from Rat 1 and about 10-fold in the Day 28 sample from Rat 2 compared to baseline samples, however, no unusual elevation in the ADA assay signal was observed in these samples, indicating that target interference was mitigated. At the same time, high levels of ADA were detected in both animals beginning at Day 85, indicating that the addition of the two target blocking reagents and the slightly basic pH assay conditions did not interfere with the detection of ADA (FIG. 6B).

Mild Basic pH Together with Target Blocking Reagents Inhibit the Binding of Target to the Drug To understand why mild basic pH and target blocking reagents can help mitigate the target interference in the clinical samples, Octet experiments were performed to test the binding of the target to the drug under different pH conditions, with or without target blocking reagents. The results are shown in FIG. 7A. As seen from the binding association curves, in the absence of MsAb2 and MsSR, the response was slightly lower at pH 8.2 compared to pH 7.3, indicating that the association between the target and the drug is slightly impacted by assay pH. However, a faster dissociation rate at pH 8.2 was observed compared to pH 7.3, indicating the binding affinity between the target and the drug is weaker at pH 8.2. At pH 7.3, in the presence of MsAb2 and MsSR, a faster dissociation rate was also observed, similar to the basic pH alone. However, the presence of the target blocking reagents also significantly impacted the association of the target to the drug. Finally, the complete inhibition of the binding is achieved with the combination of MsAb2 and MsSR at pH 8.2. The pH-dependent differences in binding are potentially attributed to either the target conformational change at mild basic pH or better binding of the target blocking reagents to the target at pH 8.2, therefore inhibiting the association of the target to the drug.

Figure 7B:
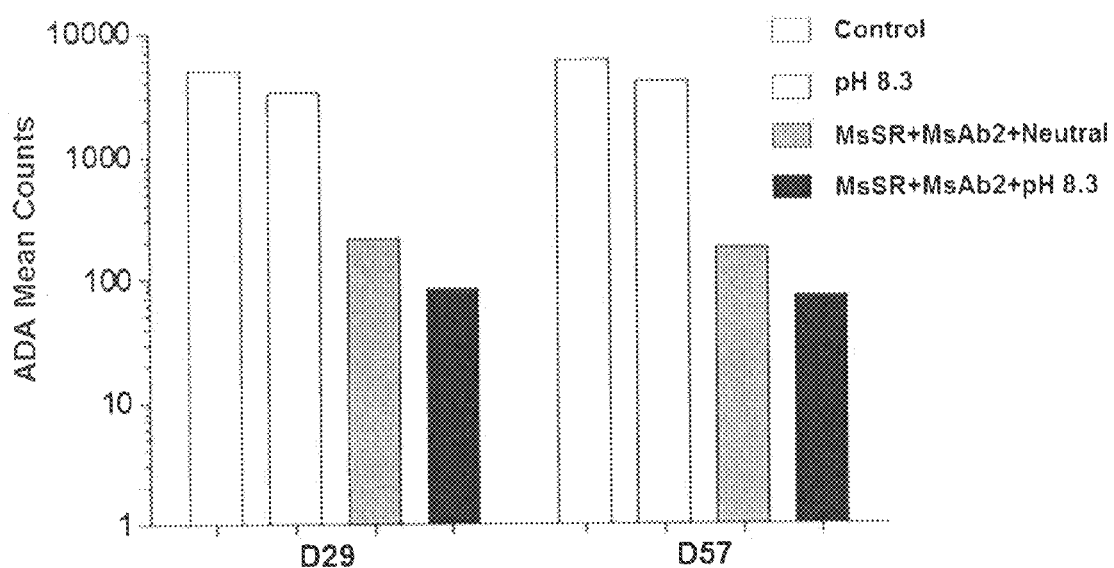

These binding data further support the ADA assay data, which shows that the basic pH alone can partially inhibit the target-mediated signal in the clinical samples. While the combination of MsAb2 and MsSR at neutral pH significantly inhibits the target-mediated signal, complete inhibition of the target interference is only obtained with the combination of MsAb2, MsSR and pH 8.3 (FIG. 7B).

Ligand Binding Assays (LBAs) are highly susceptible to interfering molecules that can confound assay results by either generating artificial signals or blocking desired assay interactions. Target interference is a common issue and can be difficult to overcome due to its specificity to the drug and the highly variable biology of each target protein. Target usually forms tight complexes with drug and its binding proteins in circulation which may be difficult to disrupt. In addition, target levels can increase to relatively high levels in circulation due to formation of target:drug and target: binding protein complexes or by feedback mechanisms inherent to the biological pathway. In ADA bridging assays, the presence of dimeric or multimeric targets can lead to false positive results and confound the evaluation of immunogenicity. This impact can be exacerbated by acid dissociation, a commonly used strategy to increase the drug tolerance in ADA assays, which can also potentially disrupt target-containing complexes, releasing the target and resulting in target-mediated false positive signals. Therefore, careful consideration must be taken during assay development, weighing the benefit of each strategy against the risk of introducing a potential artifact to the assay. Based on the biology, target-specific approaches need to be evaluated to mitigate its interference in the assay.

Pre-treatment with target blocking antibodies (as single antibodies or in combination), receptors, co-factors as well as target binding proteins can be used to mitigate target interference. In addition, assay pH can also be altered to mitigate target interference, by either directly affecting the dimeric or multimeric target or by changing the drug binding affinity to the target. Furthermore, it is important to evaluate the efficacy of the target mitigation strategy/assay format chosen by testing actual post-dose samples, since the native target protein in serum samples may behave differently than its recombinant version. The use of PK data and target levels can also be helpful in distinguishing a real ADA response from target mediated signals.

The addition of target blocking reagents can be used to mitigate target interference. However, in the case of antibody therapeutics, it must be ensured that these reagents do not share similar CDR sequences to the drug (in the case of anti-target antibodies) or contain human IgG constant sequences (in the case of antibodies, receptors and binding proteins), since these shared sequences may reduce the detection of ADAs specific to these sequences. Finally, the use of low-affinity ADA positive animal samples, with a polyclonal response to the drug, can be instrumental to ensure that true low affinity, low titer ADA responses, whose detection is more likely to be impacted by modifications to the assay, can still be detected under the final assay conditions.

In this disclosure, the drug target is a homodimer that forms multiple inactive complexes with its inhibitory binding proteins in circulation. While acid-dissociation increases the Drug Tolerance Limit (DTL) of the ADA assay, it will release the target bound to the drug and target bound to its inhibitory binding proteins. The released target will result in target interference in the ADA assay. Furthermore, treatment of mice with drug up-regulates target expression. Western blot analysis with antibodies specific to the precursors and to the mature form of the target showed that different forms of the target were up-regulated in mice 28 days after drug injection. Therefore, a robust ADA assay with as much target tolerance as possible is needed.

By including a target blocking antibody (HuAb1) and mild basic pH assay conditions (pH 8.3), the inventors were able to obtain high tolerance levels to recombinant target protein. The assay was optimized to add a second target blocking antibody HuAb2. This significantly improved target tolerance, and the rate of positivity was greatly reduced in clinical study samples. Further optimizations in the assay were made by replacing the HuAb1 anti-target antibody. Since HuAb1 shares some Complementary Determining Region (CDR) sequences with the drug, it could potentially bind anti-drug ADAs thus reducing ADA detection. Therefore, the external portion of the target receptor fused to a human IgG Fc (HuSR) was used in place of HuAb1. In combination with HuAb2, HuSR was able to block target interference as well as the HuAb1/HuAb2 combo. Subsequently, the Fc domains of HuSR and the entire constant region of HuAb2 were converted from human to mouse (MsAb2 and MsSR) to further reduce possible interference in ADA detection. Characterization experiments using the Octet system indicated that the binding of the target to the drug is inhibited by mild basic pH or the presence of anti-target blocking reagents alone. However, the complete inhibition of the binding is achieved with the combination MsAb2, MsSR and mild basic pH. Analysis of low-titer ADA positive bleeds from immunized rabbits and known ADA positive samples from nonclinical studies in rats confirmed the ability of the assay to detect ADA-positive samples and the minimal impact of basic pH and target blocking reagents on ADA detection.

These findings provide alternative strategies to overcome target interference in bridging immunogenicity assays when standard target blocking antibodies are ineffective.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

The invention claimed is:

1. A method for determining the presence of an anti-drug antibody (ADA) against a drug in a serum sample using an ADA bridging immunoassay, comprising
    contacting the serum sample with
        a capture drug labelled with a first label;
        a detection drug labelled with a second label;
        a drug target blocking reagent; and
        a second drug target blocking reagent;
    incubating the serum sample, under mild basic pH assay conditions, with the capture drug, the detection drug, the drug target blocking reagent, and the second drug target blocking reagent,
    allowing the capture drug and the detection drug to bind the ADA,
    allowing the drug target blocking reagent and the second drug target blocking reagent to bind to the drug target present in the sample,
    and detecting the ADA in the serum sample by performing the ADA bridging immunoassay,
    thereby mitigating drug target interference in the ADA bridging immunoassay,
    wherein the capture drug and detection drug are a human therapeutic monoclonal antibody or a humanized therapeutic monoclonal antibody, and wherein the capture drug and the detection drug each bind the anti-drug antibody,
wherein the drug target blocking reagent and the second drug target blocking reagent are a drug target blocking antibody or a drug target blocking reagent comprising an extracellular portion of a receptor fused to an IgG Fc domain, wherein the receptor binds the drug target,
wherein the drug target blocking reagent and the second drug target blocking reagent are different,
wherein the serum sample is pretreated with acid, and
wherein the mild basic pH is between about pH 7.5 and about pH 9.5.

2. The method of claim 1, wherein the drug target is a ligand to a receptor.

3. The method of claim 1, wherein the portion of the receptor is an extracellular portion of the receptor.

4. The method of claim 1, wherein the IgG Fc domain is a mouse IgG Fc domain.

5. The method of claim 1, wherein the IgG Fc domain is a human IgG Fc domain.

6. The method of claim 1, wherein the second drug target blocking antibody comprises a mouse constant region.

7. The method of claim 1, wherein the human or humanized therapeutic monoclonal antibody is being evaluated in a clinical trial.

8. The method of claim 1, wherein the drug target is a soluble or shed multimeric drug target.

9. The method of claim 1, wherein the drug target is a homodimeric drug target.

10. The method of claim 1, wherein the mild basic pH assay conditions comprise conditions of a pH between about 8.3 to about 8.9.

11. The method of claim 10, wherein the mild basic pH assay conditions comprise conditions of a pH of about 8.3.

12. The method of claim 10, wherein the mild basic pH assay conditions comprise conditions of a pH of about 8.9.

13. The method of claim 1, wherein the serum sample is a human serum sample.

14. The method of claim 1, wherein the serum sample is from a subject being treated with the drug.

15. The method of claim 1, wherein the incubating is done at room temperature.

16. The method of claim 1, wherein the anti-drug antibody (ADA) bridging immunoassay is a high-throughput assay.

17. The method of claim 1, wherein the capture drug is attached to a solid surface.

18. The method of claim 17, wherein the solid surface is a microtiter plate.

19. The method of claim 17, wherein the solid surface is coated with streptavidin.

20. The method of claim 1, wherein the capture label is selected from the group consisting of a biotin label, a Protein A label, a Protein G label, and a glutathionine S-transferase (GST) label.

21. The method of claim 1, wherein the second label is selected from the group consisting of a ruthenium label, a radiologic label, a photoluminescent label, a chemiluminescent label, a fluorescent label, an electrochemiluminescent label, and an enzyme label.

22. A method for determining the presence of an anti-drug antibody (ADA) against a drug in a serum sample using an ADA bridging immunoassay, comprising
contacting the serum sample with
a capture drug labelled with a first label;
a detection drug labelled with a second label;
a first drug target blocking antibody; and
a second drug target blocking antibody,
incubating, under mild basic pH assay conditions, the capture drug, the detection drug, the first drug target blocking antibody, and the second drug target blocking antibody,
allowing the capture drug and the detection drug to bind the ADA,
allowing the first drug target blocking antibody and the second drug target blocking antibody to bind to the drug target present in the sample,
and detecting the ADA in the serum sample by performing the ADA bridging immunoassay,
thereby mitigating drug target interference in the ADA bridging immunoassay,
wherein the capture drug and the detection drug are a human therapeutic monoclonal antibody or a humanized therapeutic monoclonal antibody, and wherein the capture drug and the detection drug each bind the anti-drug antibody,
wherein the first drug target blocking antibody and second drug target blocking antibody are different,
wherein the serum sample is pretreated with acid, and
wherein the mild basic pH is between about pH 7.5 and about pH 9.5.

23. A method for determining the presence of an anti-drug antibody (ADA) against a drug in a serum sample using an ADA bridging immunoassay, the method comprising
contacting the serum sample with
a capture drug labelled with a first label;
a detection drug labelled with a second label;
a drug target blocking reagent comprising an extracellular portion of the receptor fused to an IgG Fc domain; and
a drug target blocking antibody,
incubating, under mild basic pH assay conditions, the capture drug, the detection drug, the drug target blocking reagent, and the drug target blocking antibody,
allowing the capture drug and the detection drug to bind the ADA,
allowing the drug target blocking reagent and the drug target blocking antibody to bind to the drug target present in the sample,
and detecting the ADA in the serum sample by performing the ADA bridging immunoassay,
thereby mitigating drug target interference in the ADA bridging immunoassay,
wherein the capture drug and detection drug are a human therapeutic monoclonal antibody or a humanized therapeutic monoclonal antibody, and wherein the capture drug and the detection drug each bind the anti-drug antibody,
wherein the serum sample is pretreated with acid, and
wherein the mild basic pH is between about pH 7.5 and about pH 9.5.

* * * * *